(12) United States Patent
Abdelgany

(10) Patent No.: US 7,442,197 B2
(45) Date of Patent: Oct. 28, 2008

(54) VARIABLE DEPTH DRILL GUIDE

(75) Inventor: Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 182 days.

(21) Appl. No.: 11/280,167

(22) Filed: Nov. 16, 2005

(65) Prior Publication Data
US 2006/0264955 A1    Nov. 23, 2006

Related U.S. Application Data

(60) Provisional application No. 60/683,707, filed on May 23, 2005.

(51) Int. Cl.
*A61B 17/58* (2006.01)
*A61B 17/60* (2006.01)

(52) U.S. Cl. .................................................. 606/96

(58) Field of Classification Search .................. 606/86, 606/97, 98, 96, 87, 88, 79; 408/72 R, 81
See application file for complete search history.

(56) References Cited

U.S. PATENT DOCUMENTS

| | | | |
|---|---|---|---|
| 5,112,335 A * | 5/1992 | Laboureau et al. ............ 606/88 |
| 5,234,434 A | 8/1993 | Goble et al. | |
| 5,507,801 A * | 4/1996 | Gisin et al. ................... 606/86 |
| 5,746,743 A * | 5/1998 | Greenberg .................... 606/96 |
| 5,899,908 A | 5/1999 | Kuslich et al. | |
| 6,203,543 B1 | 3/2001 | Glossop | |
| 6,286,401 B1 * | 9/2001 | Hajianpour .................. 81/453 |
| 7,060,068 B2 * | 6/2006 | Tromanhauser et al. ....... 606/61 |
| 2003/0233098 A1* | 12/2003 | Markworth ................... 606/96 |

* cited by examiner

Primary Examiner—Pedro Philogene
(74) Attorney, Agent, or Firm—Mohammad S. Rahman, Esq; Gibb & Rahman, LLC

(57) ABSTRACT

A variable depth drill guide assembly and a method of controlling a depth of a drill insertion into a bone using the variable depth drill guide assembly, wherein the assembly comprises a shaft; an outer sleeve connected to the shaft, wherein the outer sleeve comprises slots; a tip connected to the outer sleeve; an inner sleeve slidably mounted in the outer sleeve; and a spring engaging the inner sleeve and the outer sleeve. Moreover, the inner sleeve is preferably adapted to control a depth of a drill insertion into a bone. Additionally, the inner sleeve preferably comprises a stop adapted to engage the slots of the outer sleeve. Furthermore, the spring may be adapted to provide spring loading for the inner sleeve.

20 Claims, 12 Drawing Sheets

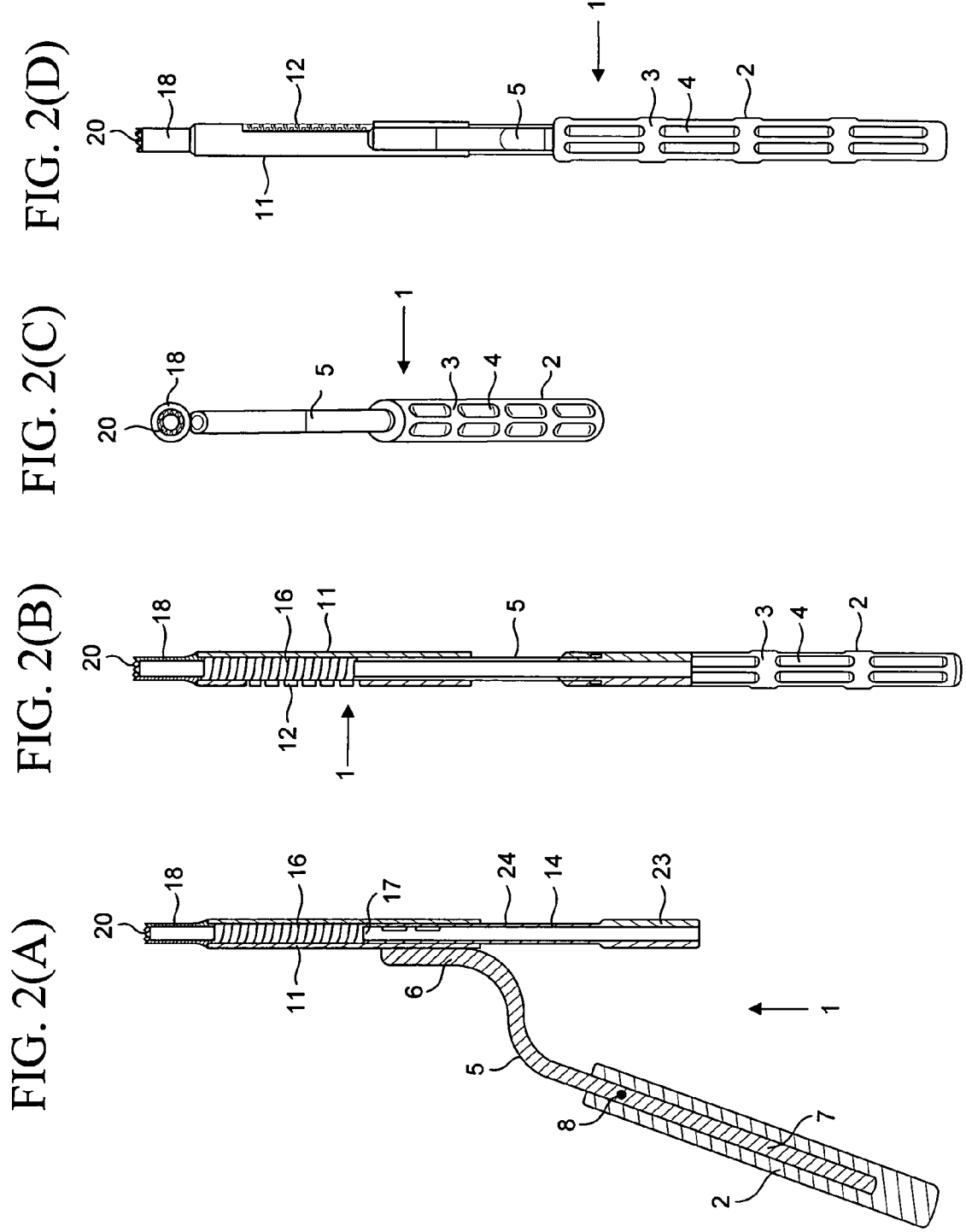

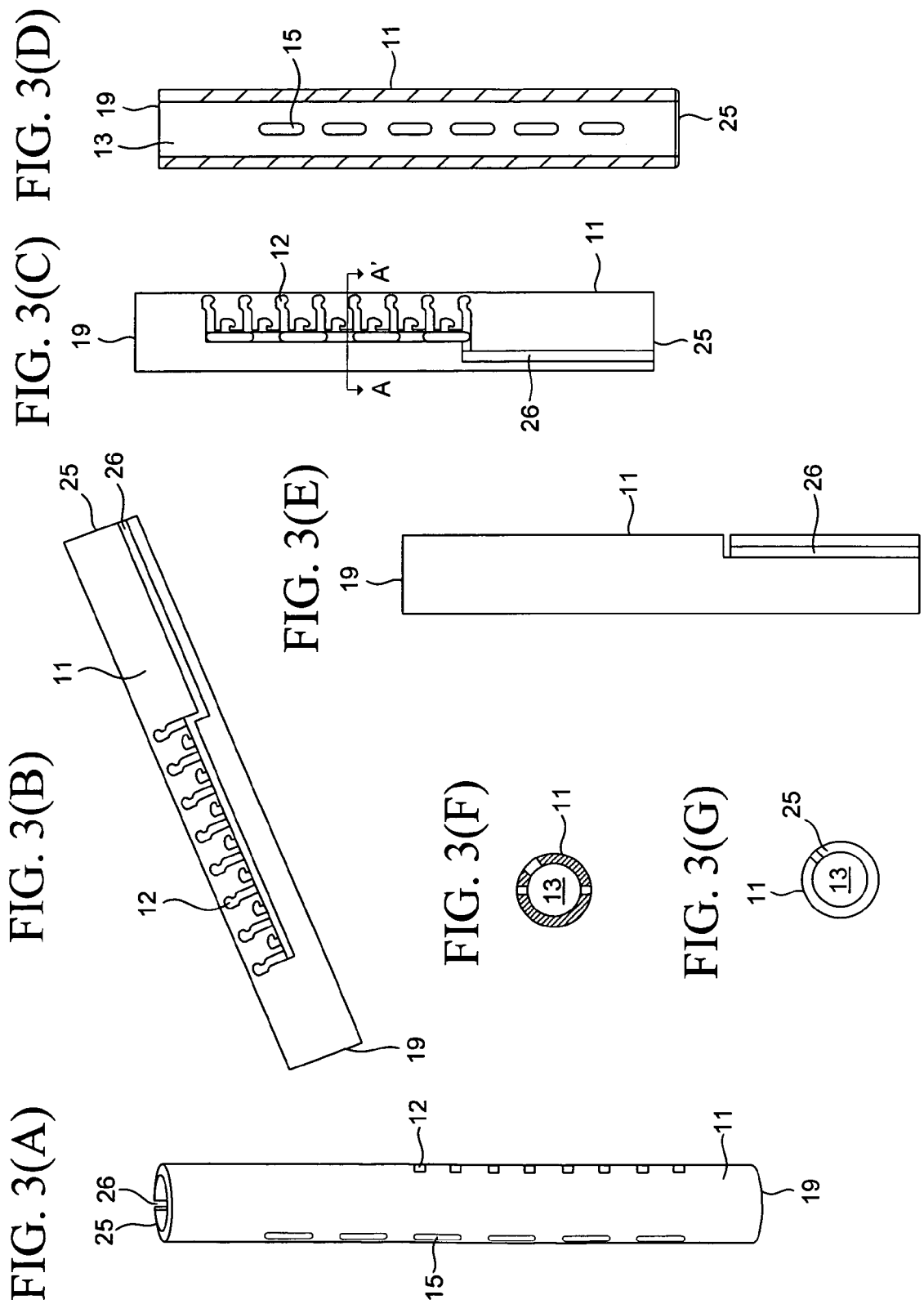

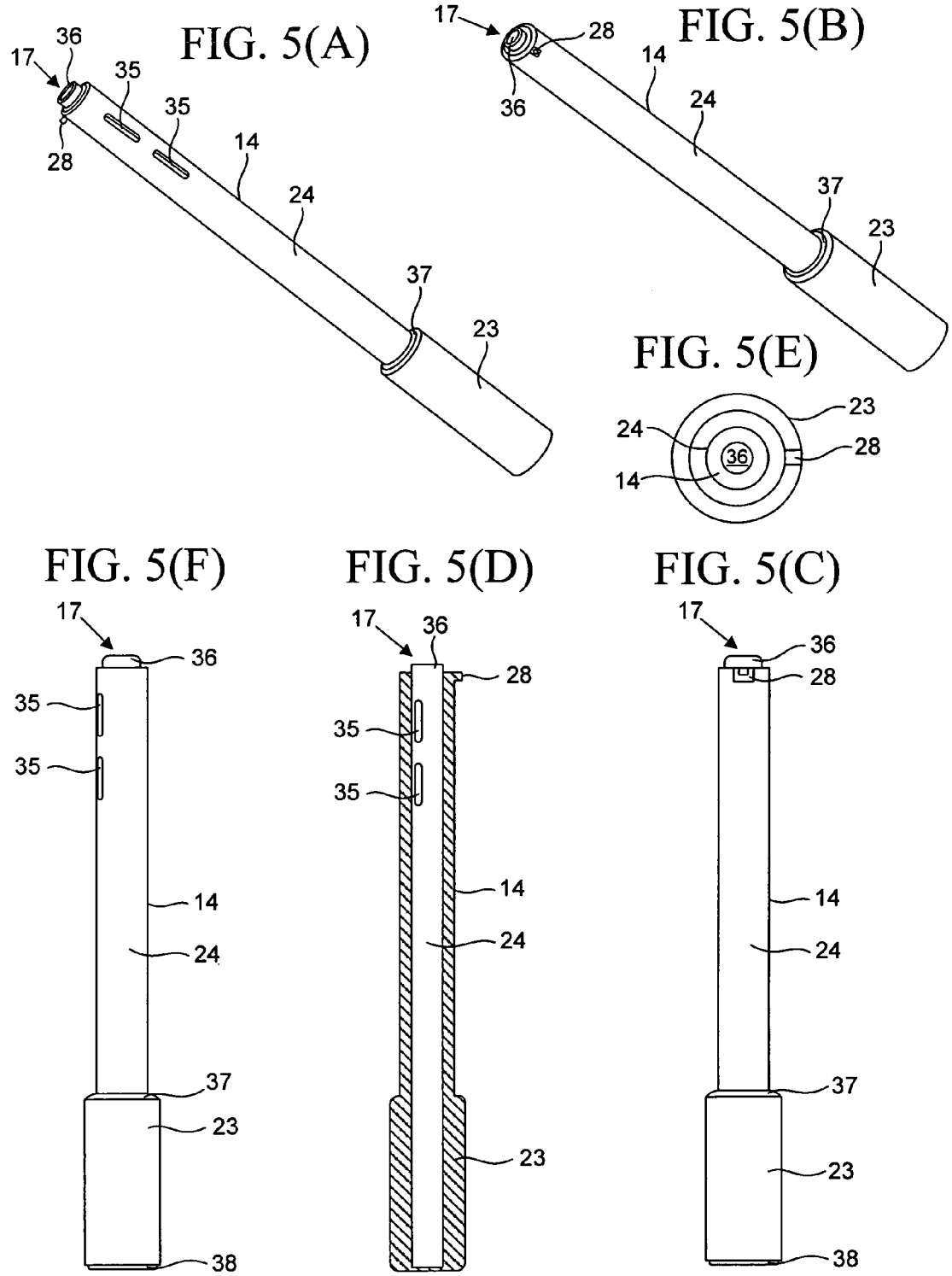

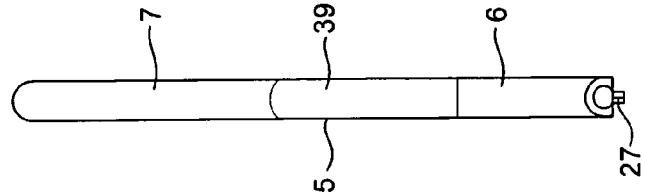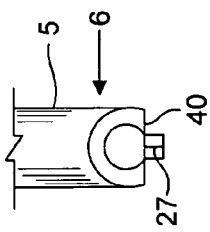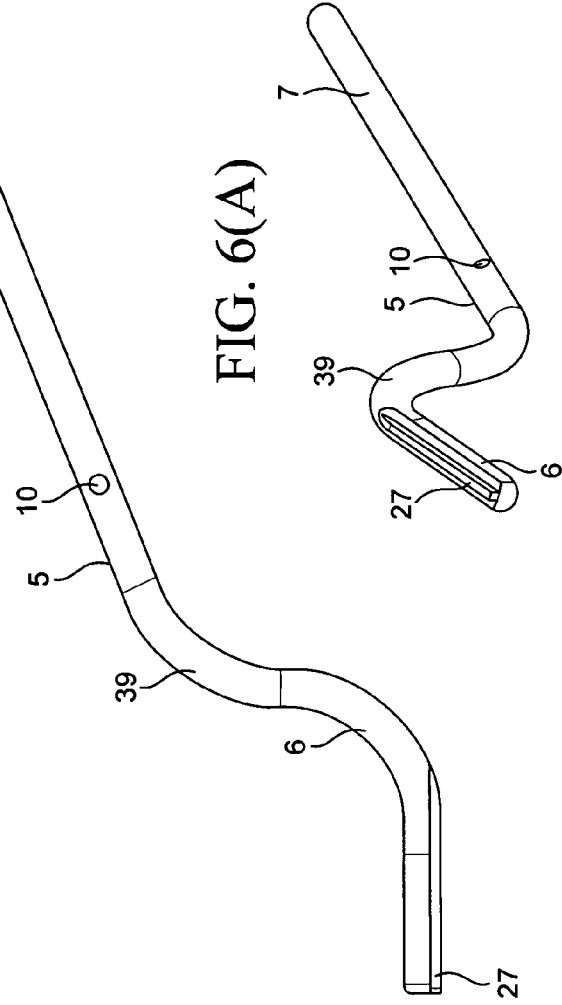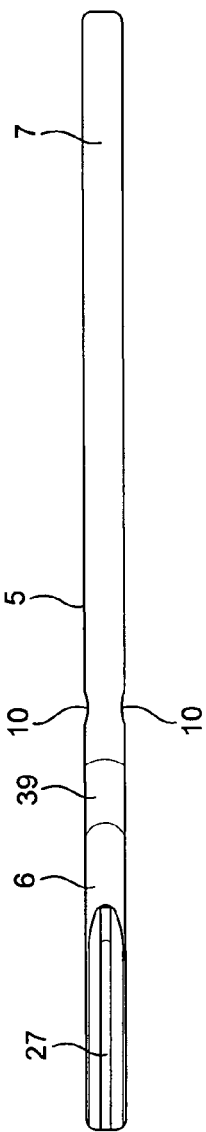

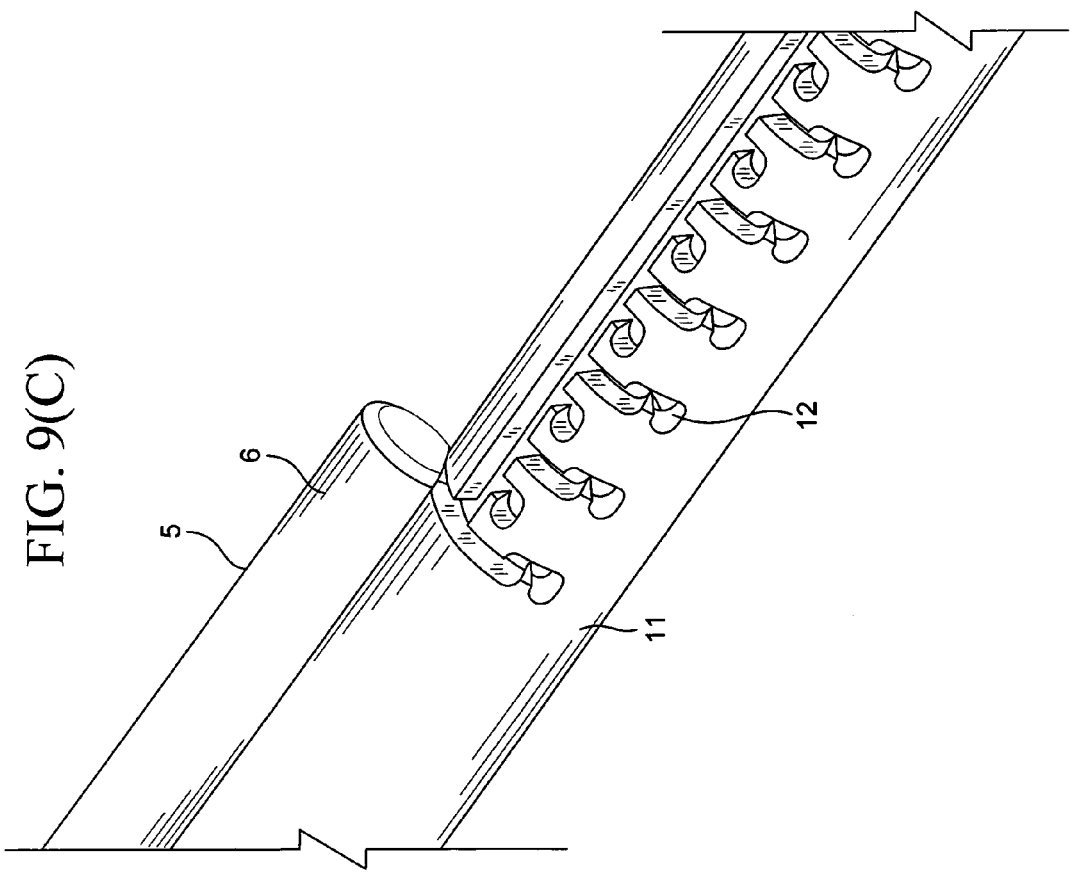

VARIABLE DEPTH DRILL GUIDE

CROSS-REFERENCE TO RELATED APPLICATION

This application claims the benefit of U.S. Provisional Patent Application No. 60/683,707 filed on May 23, 2005, the contents of which, in its entirety, is herein incorporated by reference.

BACKGROUND

1. Field of the Invention

The embodiments herein generally relate to medical devices, and, more particularly, to medical devices used in spinal surgeries.

2. Description of the Related Art

Most conventional surgical drill guides generally do not offer various depth and positive settings to control accurate drilling depth. Threaded mechanisms within conventional drill guides are generally not positive due to the fact that rotary drills tend to destabilize or change the preset depth in the threaded adjustable depth drill guides. Other systems such as the one described in U.S. patent application Ser. No. 2003/0233098 A1, the complete disclosure of which in its entirety is herein incorporated by reference generally offer variable depth guides, but they are generally expensive and complicated to use, as well as possibly prone to failure due to fatigue because they typically depend on a spring portion that loses elasticity during normal use and hot steam autoclaving cycles that are necessary for cleaning surgical tools. Without a positive safe variable depth drill guide, one has to significantly increase drill bit inventory of multiple drill lengths to accomplish the same task. Other conventional designs generally incorporate too many parts such as multiple inner tubes with one or more outer tubes to provide a variety of depth.

Generally, the conventional drill guides may have the following attributes: (1) generally are less than positive designs; (2) generally are difficult to set depth and usage may require two hands; (3) typically the depth control is effected by a rotary drill or tool, making them potentially dangerous; (4) generally tend to rely on visual markings for depth as opposed to a firm stop to control depth; (5) generally require a multitude of inner tubes and/or drills to accomplish accurate depth drilling; and (6) typically tend to drill too deep in the human spine, which may cause death or severe nerve injury to the patient. Therefore, there remains a need for a novel variable depth drill guide capable of controlling the depth of drilling during spinal surgeries and which generally overcomes the limitations of the conventional drill guides.

SUMMARY

In view of the foregoing, an embodiment herein provides a variable depth drill guide assembly comprising a shaft; an outer sleeve connected to the shaft, wherein the outer sleeve comprises slots; a tip connected to the outer sleeve; an inner sleeve slidably mounted in the outer sleeve; and a spring engaging the inner sleeve and the outer sleeve. The assembly may further comprise a hole in each of the handle and the shaft; and a pin dimensioned and configured to engage the hole in each of the handle and the shaft, wherein the pin is adapted to connect the shaft to the handle. The shaft may comprise a pair of straight ends connected by a curved portion, wherein the outer sleeve may be connected to one of the straight ends of the shaft. In one embodiment, the slots are configured at substantially every 2 millimeters on the outer sleeve. Preferably, the tip comprises a plurality of appendages. Moreover, the inner sleeve is preferably adapted to control a depth of a drill insertion into a bone. Additionally, the inner sleeve preferably comprises a stop adapted to engage the slots of the outer sleeve. Furthermore, the spring may be adapted to provide spring loading for the inner sleeve. The assembly may further comprise a handle connected to the shaft. Also, in one embodiment the assembly may further comprise a handle mounted over one of the straight ends of the shaft. Preferably, the inner sleeve and the outer sleeve each comprise cleaning holes.

Another embodiment provides an assembly comprising a handle; a shaft comprising a straight end and a curved portion; a pin adapted to connect the handle to the shaft; an outer sleeve comprising slots configured in the outer sleeve, wherein the outer sleeve is connected to the shaft; a tip connected to the outer sleeve, wherein the tip comprises a plurality of appendages; an inner sleeve slidably mounted in the outer sleeve and adapted to control a depth of a drill insertion into a bone, wherein the inner sleeve comprises a stop; and a spring adapted to provide spring loading for the inner sleeve, wherein the slots are preferably configured at substantially every 2 millimeters on the outer sleeve. Preferably, the handle mounts over the straight end of the shaft. Moreover, the stop of the inner sleeve is preferably adapted to engage the slots of the outer sleeve. In one embodiment, the inner sleeve and the outer sleeve each comprise cleaning holes. Additionally, the stop is preferably adapted to prevent over-drilling of the drill in the bone. Furthermore, the appendages on the tip are preferably adapted to prevent slippage of the tip on a bone surface.

Another embodiment provides a method of controlling a depth of a drill insertion into a bone using a variable depth drill guide assembly comprising an outer sleeve, wherein the outer sleeve comprises slots; a tip connected to the outer sleeve; an inner sleeve comprising a stop and mounted in the outer sleeve; and a spring engaging the inner sleeve and the outer sleeve, wherein the method comprises simultaneously depressing and rotating the inner sleeve until the stop of the inner sleeve mates with a corresponding slot in the outer sleeve; pushing the tip into the bone; inserting a drill into the inner sleeve; the drill contacting the inner sleeve as the drill approaches a final position within the inner sleeve; the inner sleeve resisting force asserted by the drill; and the force overcoming the resistance from the inner sleeve.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 2(A) through 2(D) illustrate schematic diagrams of the drill guide shaft and handle of the variable depth drill guide assembly of FIG. 1 according to an embodiment herein;

FIGS. 3(A) through 3(G) illustrate schematic diagrams of the drill guide outer sleeve of the variable depth drill guide assembly of FIG. 1 according to an embodiment herein;

FIGS. 5(A) through 5(F) illustrate schematic diagrams of the drill guide inner sleeve of the variable depth drill guide assembly of FIG. 1 according to an embodiment herein;

FIGS. 6(A) through 6(E) illustrate schematic diagrams of the drill guide shaft of the variable depth drill guide assembly of FIG. 1 according to an embodiment herein;

FIG. 9(C) illustrates an isolated view of the drill guide outer sleeve of the variable depth drill guide assembly of FIG. 1 according to an embodiment herein.

DETAILED DESCRIPTION OF PREFERRED EMBODIMENTS

Figure 1:
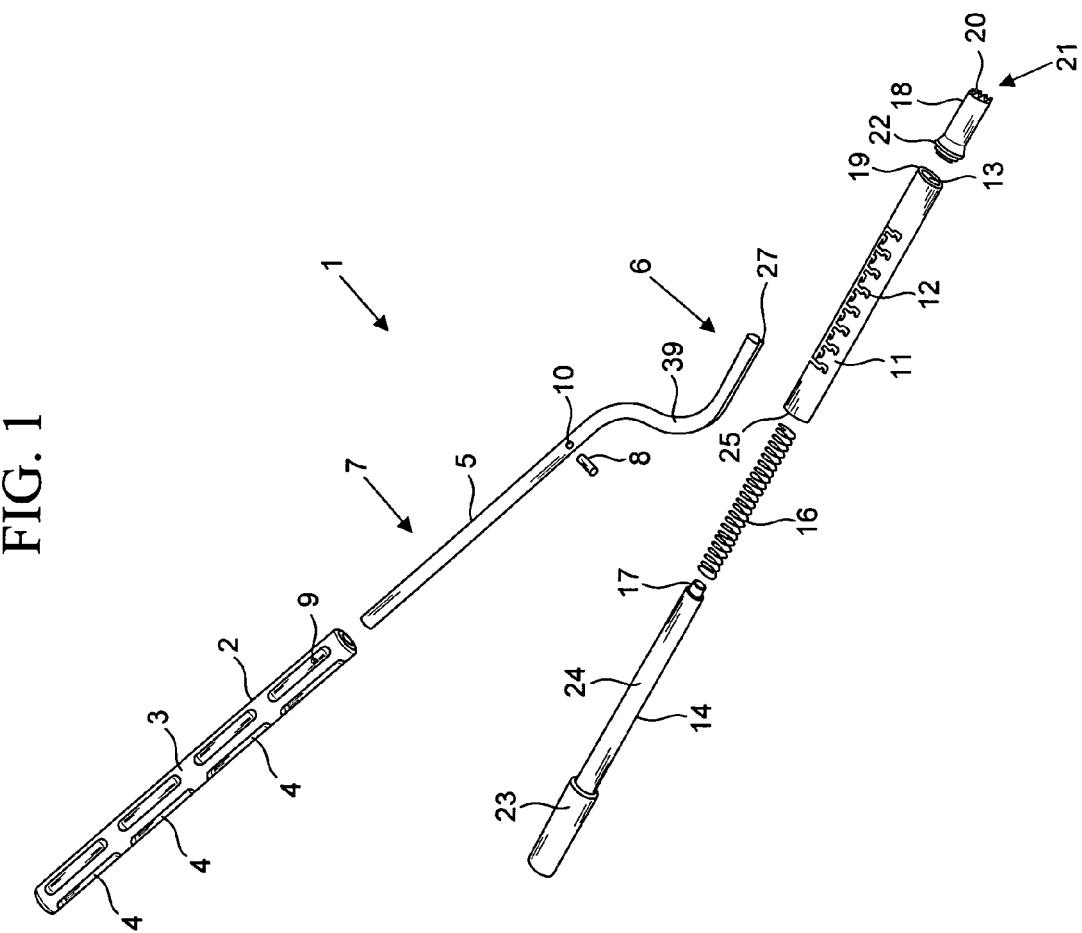
FIG. 1 illustrates an exploded view of a variable depth drill guide assembly according to an embodiment herein.
Figure 4A:
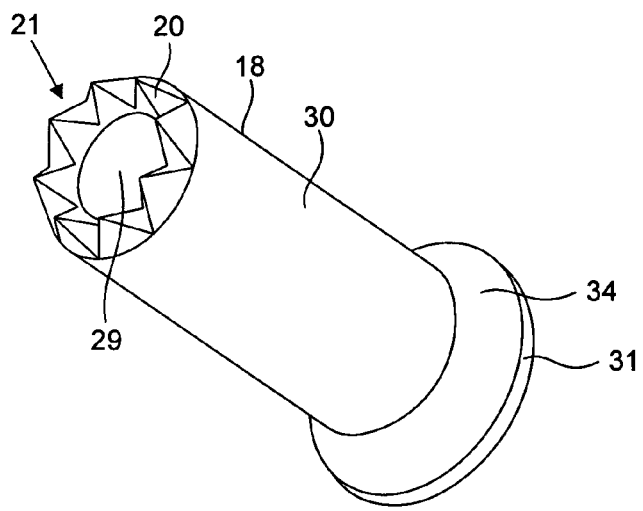
FIGS. 4(A) through 4(D) illustrate schematic diagrams of the drill guide tip of the variable depth drill guide assembly of FIG. 1 according to an embodiment herein.
Figure 4B:
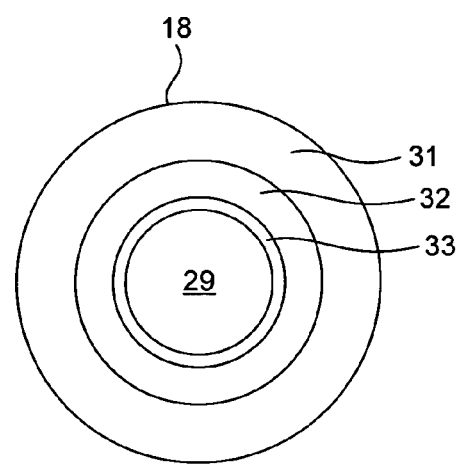
Figure 4C:
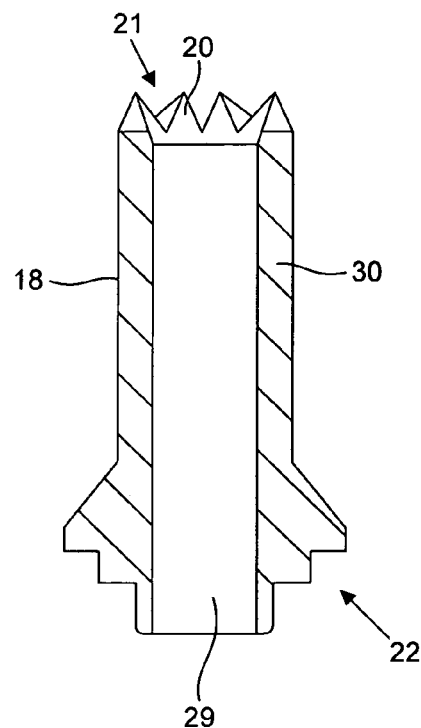
Figure 4D:
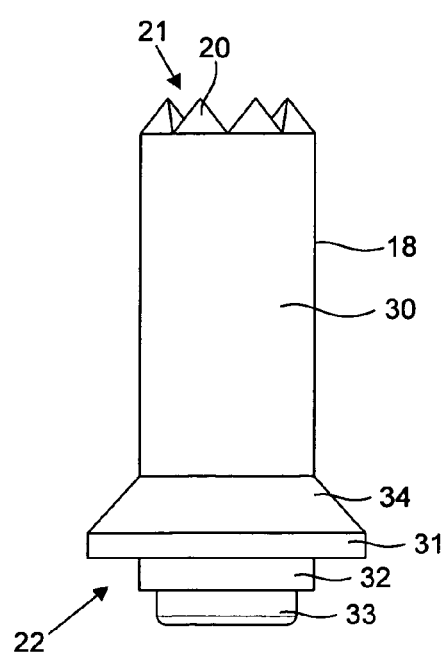
Figure 7A:
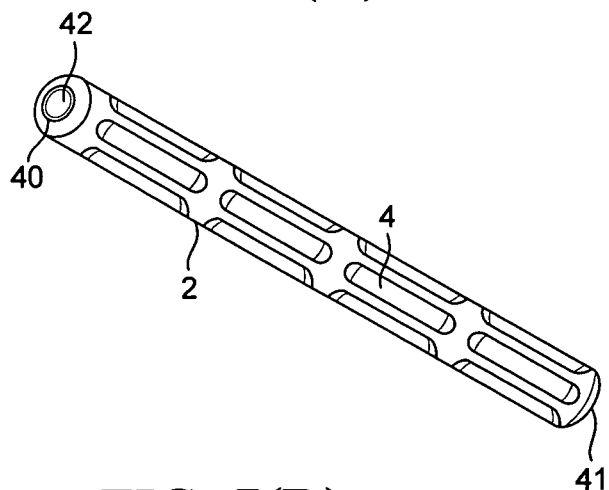
FIGS. 7(A) through 7(D) illustrate schematic diagrams of the drill guide handle of the variable depth drill guide assembly of FIG. 1 according to an embodiment herein.
Figure 7C:
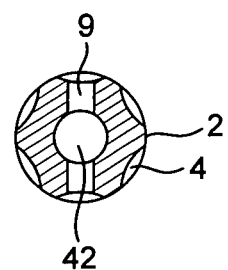
Figure 7B:
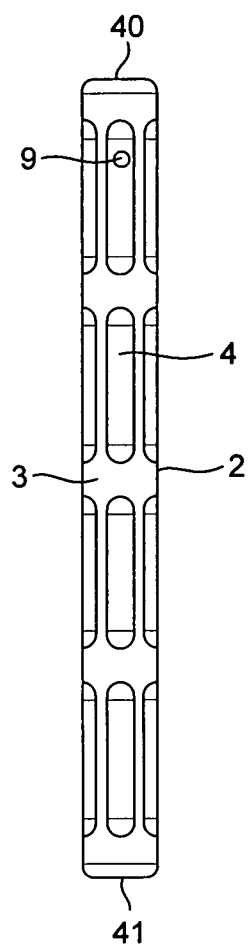
Figure 7D:
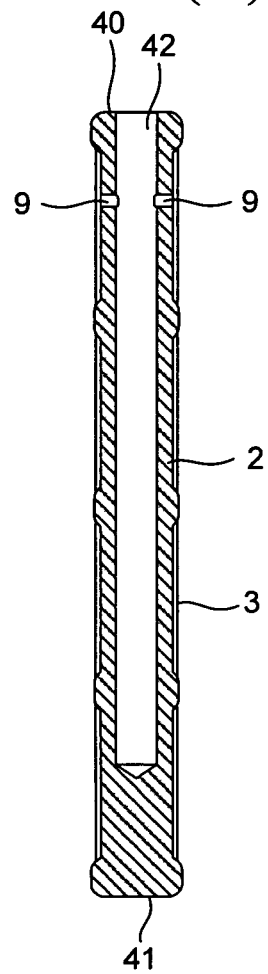
Figure 8A:
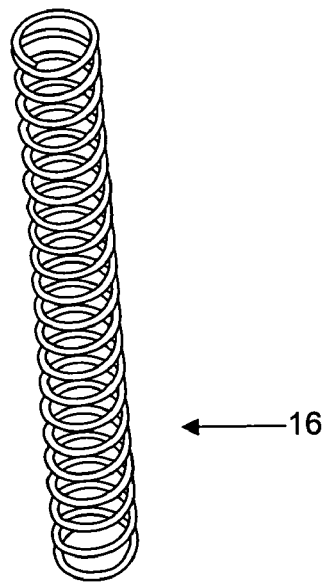
FIGS. 8(A) through 8(C) illustrate schematic diagrams of the drill guide spring of the variable depth drill guide assembly of FIG. 1 according to an embodiment herein.
Figure 8B:
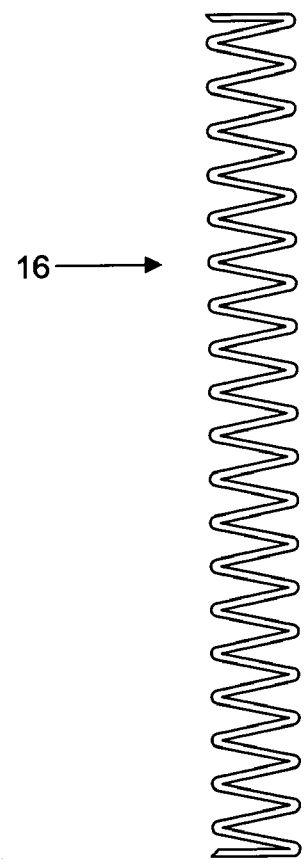
Figure 8C:
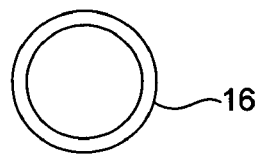

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a novel variable depth drill guide capable of controlling the depth of drilling during spinal surgeries and which generally overcomes the limitations of the conventional drill guides. The embodiments herein achieve this by providing a mechanism to control the depth of drilling with a drill guide at variable increments accurately and consistently in a positive manner during orthopedic or spine surgery. Preferably, the embodiments herein will be generally used in orthopedic surgery, and more specifically for spine surgery in the posterior spine. Referring now to the drawings, and more particularly to FIGS. 1 through 10, there are shown preferred embodiments.

FIGS. 1 through 8(C) illustrate a variable depth drill guide assembly 1 and its various components according to an embodiment herein. As shown in the perspective view of FIG. 1, the assembly 1 generally comprises a drill guide handle 2 having an outer body 3 that is configured for optimum visibility and function and includes grooves 4 on the outer body 3 thereof for a positive grip for a user. The handle 2 is generally hollow and mounts over a drill guide shaft 5 that is angled for optimized function and visibility. The drill guide shaft 5 includes a pair of generally linear ends 6, 7 and a generally curved (angled) portion 39 connecting the ends 6, 7. A pin 8 connects the handle 2 to the drill guide shaft 5, whereby each of the outer body 3 of the handle 2 and the drill guide shaft 5 have holes 9, 10, respectively, configured therein to permit the pin 8 to connect the handle 2 to the drill guide shaft 5. The assembly 1 further includes a drill guide outer sleeve 11 comprising a hollow inner portion 13 and S-shaped slots 12 configured for interfacing with a drill guide inner sleeve 14.

As shown in more detail in FIGS. 3(A) through 3(G), the outer sleeve 11 comprises graduated slots 12 approximately every 2 mm thereby permitting accurate drill depth. The slots 12 provide a positive lock with the inner sleeve 14 to prevent slippage and over-drilling. Preferably, the outer sleeve 11 is permanently assembled with cleaning holes 15 (more clearly shown in the cross-sectional view of FIG. 3(D)) to allow for sterilization of the assembly 1 without requiring disassembly/reassembly of the various components of the assembly 1. The outer sleeve 11 comprises a top end 25 and a bottom end 19. An elongated groove 26 is configured in the outer sleeve 11, and preferably beginning at the top end 25 of the outer sleeve 11 and extending nearly one half of the way down the outer sleeve 11 up to the point where the slots 12 begin. FIG. 3(F) is a cross-sectional view taken along line A-A' of FIG. 3(C).

The inner sleeve 14 controls the depth of the drill insertion and provides a stop 28 to prevent over-drilling. The inner sleeve 14 is spring loaded for positive positioning in the outer sleeve 11. Moreover, the inner sleeve 14 is slidably mounted in the outer sleeve 11. Accordingly, a spring 16 or other appropriate bias element providing resistance is inserted in the hollow inner portion 13 of the outer sleeve 11 and engages a spring end 17 of the inner sleeve 14. The spring 16 is shown in further detail in FIGS. 8(A) through 8(C). The spring 16 provides the spring load on the inner sleeve 14 for a positive function and a tactile feel as the drill assembly 1 stops on the outer sleeve 11. The guide shaft 5 comprises an elongated guide 27 that fits into a correspondingly dimensioned groove 26 in the outer sleeve 11. Additionally, the assembly 1 comprises a drill guide tip 18 having an angled end 22 that connects to the bottom end 19 of the outer sleeve 11, wherein the drill guide tip 18 includes teeth 20 at the distal end 21 of the tip 18 to prevent slippage on the surface of a bone (not shown).

FIGS. 2(A) through 2(D) illustrate additional schematic diagrams of the variable depth drill guide assembly 1 of FIG. 1 according to an embodiment herein. FIG. 2(A) generally shows a cross-sectional view of the assembly 1 with the shaft 5 connected to the outer sleeve 11 and with the handle 2. Additionally, the inner sleeve 14, spring 16, and drill guide tip 18 are shown fully connected to the outer sleeve 11 as well. As shown in FIGS. 2(A) and 2(B), the spring 16 engages the spring-engaging end 17 of the inner sleeve 14 and the angled end 22 of the tip 18. A cross-sectional bottom view of the assembly 1 is illustrated in FIG. 2(B) and a front view of the assembly 1 is illustrated in FIG. 2(C). A top view of the assembly 1 is depicted in FIG. 2(D).

FIGS. 4(A) through 4(D) illustrate isolated schematic diagrams of the drill guide tip 18 of the variable depth drill guide assembly 1. The tip 18 also includes a hollow inner portion 29. Preferably, the angled end 22 and distal end 21 of the tip 18 are separated by a generally elongated middle portion 30. Furthermore, the teeth 20 are preferably circumferentially arranged on the distal end 21 of the tip 18. The angled end 22 may be configured as a stepped ring structure comprising a series of annular rings 31, 32, 33 formed successively on one another. For example, a bottom ring 31 may be the diametrically largest of the rings and may have a tapered lower section 34, which joins with the middle portion 30 of the tip 18. Next, a middle ring 32 is positioned on the bottom ring 31 and is diametrically dimensioned slightly smaller than the bottom ring 31. Finally, an upper ring 33 is positioned on the middle ring 32 and is diametrically dimensioned slightly smaller than the middle ring 32.

FIGS. 5(A) through 5(F) illustrate isolated schematic diagrams of the drill guide inner sleeve 14 of the assembly 1. Generally, the inner sleeve 14 has a tri-dimensioned configuration, wherein a top end 23 is generally configured to have the same diametrical configuration as the outer sleeve 11. Moreover, a substantially elongated middle portion 24 is generally configured to have the same diametrical configuration as the spring 16, whereby the middle portion 24 is preferably dimensioned to be diametrically smaller than the top end 23. Additionally, the spring-engaging end 17 comprises a generally circular tip 36, which is dimensioned and configured to have a smaller diametrical configuration than the middle portion 24, and is preferably dimensioned to fit within the diametrical constraints of the spring 16. The middle portion 24 comprises a plurality of cleaning holes 35. Also, positioned towards the spring-engaging end 17 is the stop 28, which is dimensioned and configured to engage the slots 12 of the outer sleeve 11. The top end 23 may comprise a pair of tapered ends 37, 38, wherein tapered end 37 mates with the top end 25 of the outer sleeve 14.

FIGS. 6(A) through 6(E) illustrate isolated schematic diagrams of the drill guide shaft 5 of the assembly 1. End 7 is generally configured at a longer length than end 6 such that end 7 is configured to permit the handle 2 to fit over the end 7 of guide shaft 5. End 6 comprises a lower surface 40 from which the elongated guide 27 sticks outwardly therefrom and whereby the elongated guide 27 fits into the correspondingly dimensioned groove 26 in the outer sleeve 11. The lower surface 40 of the end 6 is preferably flat to better mate with the outer sleeve 11. FIG. 6(D) illustrates an isolated view of the guide 27 and flat surface 40 of the end 6 of the shaft 5.

FIGS. 7(A) through 7(D) illustrate isolated schematic diagrams of the drill guide handle 2 of the assembly 1. Generally, the handle 2 comprises a first end 40 and a second end 41, wherein the first end 40 opens to a hollow inner portion 42 of the handle 2, which terminates at approximately three-quarters the length of the handle 2 such that the linear end 7 of the shaft 5 fits into the hollow inner portion 42 of the handle 2.

Figure 9A:
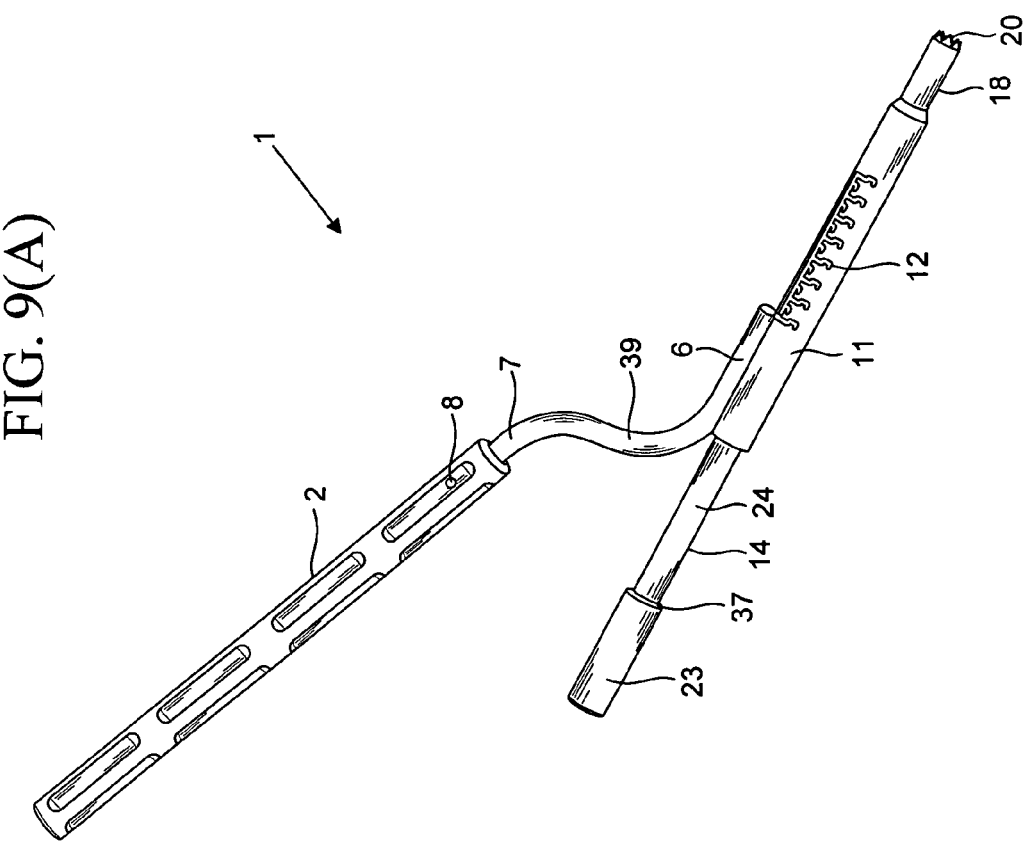
FIGS. 9(A) and 9(B) illustrate schematic diagrams of an assembled variable depth drill guide assembly in various stages of use according to an embodiment herein.
Figure 9B:
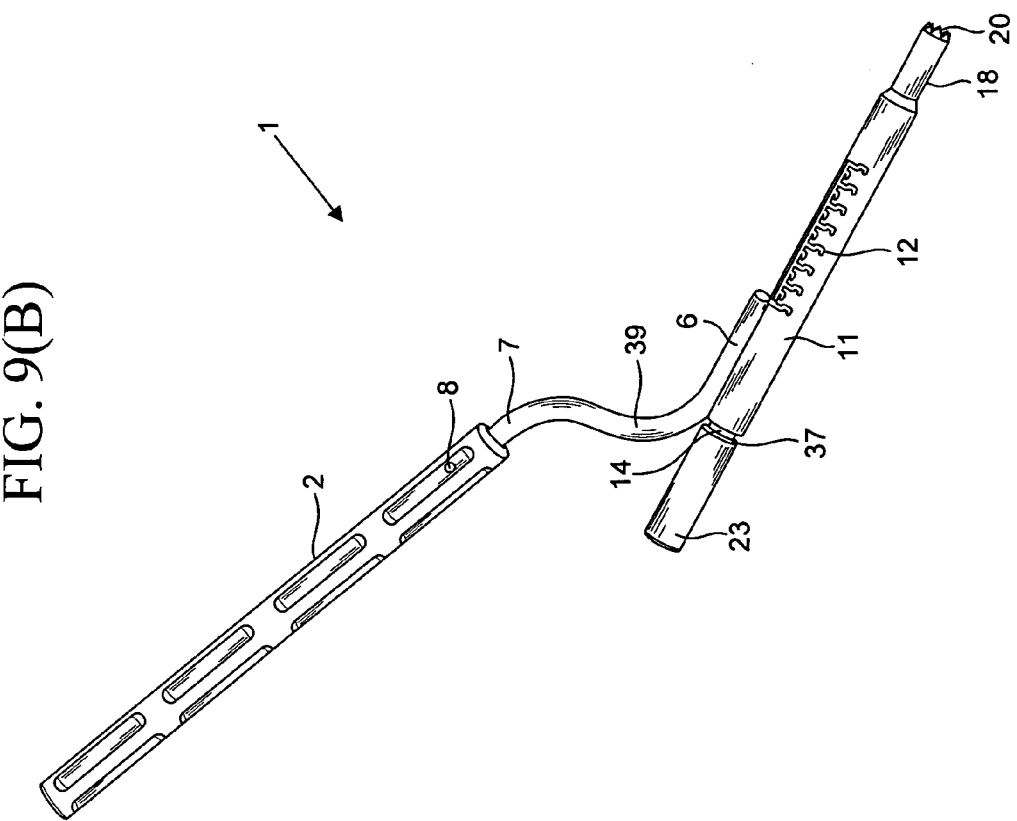

FIGS. 9(A) and 9(B) illustrate schematic diagrams of an assembled variable depth drill guide assembly 1 in various stages of use. FIG. 9(A) illustrates the assembly 1 with the inner sleeve 14 partially loaded into the outer sleeve 11 and FIG. 9(B) illustrates the assembly 1 with the inner sleeve 14 fully loaded into the outer sleeve 11. FIG. 9(C) illustrates an isolated view of the linear end 6 of the shaft 5 engaging the drill guide outer sleeve 11 of the variable depth drill guide assembly 1 of FIG. 1.

Figure 10:
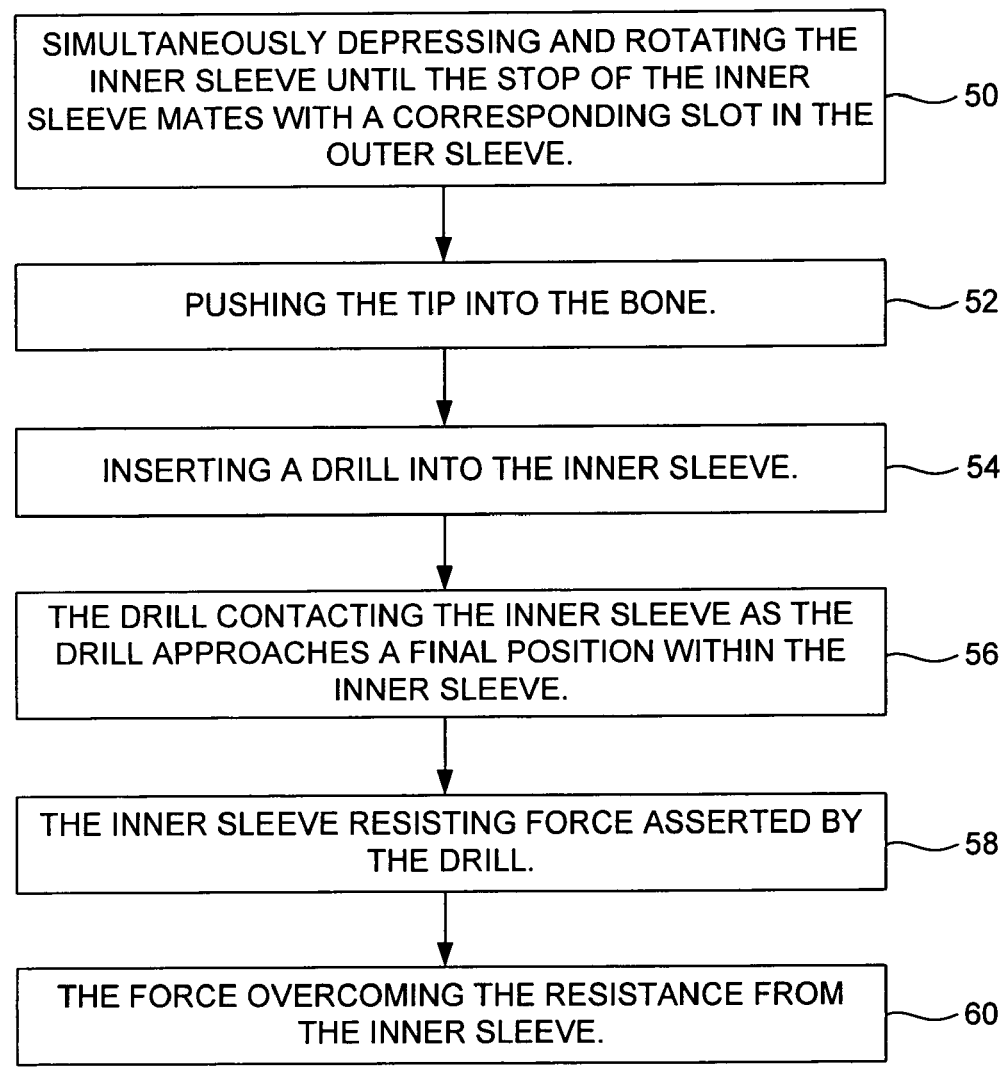
FIG. 10 is a flow diagram illustrating a preferred method according to an embodiment herein.

According to another embodiment, FIG. 10, with reference to FIGS. 1 through 9(C), is a flow diagram illustrating a method of controlling a depth of a drill insertion into a bone using a variable depth drill guide assembly 1 comprising an outer sleeve 11, wherein the outer sleeve 11 comprises slots 12; a tip 18 connected to the outer sleeve 11; an inner sleeve 14 comprising a stop 28 and mounted in the outer sleeve 11; and a spring 16 engaging the inner sleeve 14 and the outer sleeve 11, wherein the method comprises simultaneously depressing and rotating (50) the inner sleeve 14 until the stop 28 of the inner sleeve 14 mates with a corresponding slot 12 in the outer sleeve 11; pushing (52) the tip 18 into the bone (not shown); inserting (54) a drill (not shown) into the inner sleeve 14; the drill contacting (56) the inner sleeve 14 as the drill approaches a final position within the inner sleeve 14; the inner sleeve 14 resisting (58) force asserted by the drill; and the force overcoming (60) the resistance from the inner sleeve 14.

The embodiments provide an awl to create a dimple in an exposed spinal bone to break through the cortical bone and create a landmark. According to the embodiments herein, to set the depth in the drill guide assembly 1, the inner sleeve 14 is depressed while rotating it clockwise or counter clockwise until the stop 28 at the tip of the inner sleeve 14 mates with the corresponding slot 12 in the outer sleeve 11 of the drill guide assembly 1. Since most, if not all, of the drill bits function in a clockwise motion, the preset depth is held in place accurately due to the spring 16 pushing on the inner sleeve 14 and the geometry of the slot 12 on the outer sleeve 11. Next, the drill guide assembly 1 is held in one hand after it is set to control the desired depth of the hole to be drilled into the bone. The tip 18 of the guide assembly 1 is then pushed or depressed into the bone. Thereafter, the drill (not shown) is inserted through the drill guide assembly 1 and is used to cut through the bone. As the drill approaches its final position within the drill guide assembly 1, the shoulder of the drill bit (not shown) contacts the end 38 of the spring loaded drill guide inner sleeve 14. At that point, the drill guide inner sleeve 14 resists, but eventually it will be overcome by the insertion force and provide the surgeon with tactile feedback indicating that the drilling is complete.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A variable depth drill guide assembly comprising:
    an S-shaped shaft comprising:
        a curved portion;
        a pair of straight ends connected by said curved portion; and
        an elongated guide outwardly projecting along a substantially entire length of a longitudinal axis of a first one of said straight ends;
    an outer sleeve connected to said shaft, wherein said outer sleeve comprises slots;
    a tip connected to said outer sleeve;
    an inner sleeve slidably mounted in said outer sleeve, wherein said inner sleeve comprises a top end having a first diametrical configuration and a first length, a middle portion having a second diametrical configuration smaller than said first diametrical configuration and a second length longer than said first length, and a bottom end having a third diametrical configuration smaller than said second diametrical configuration and a third length shorter than said first length; and
    a spring engaging said inner sleeve and said outer sleeve.

2. The assembly of claim 1, further comprising:
    a handle connected to a second one of said straight ends of said shaft;

a hole in each of said handle and said second one of said straight ends of said shaft; and a pin that engages said hole in each of said handle and said second one of said straight ends of said shaft, wherein said pin connects said second one of said straight ends of said shaft to said handle.

3. The assembly of claim 1, wherein said straight end comprising said elongated guide is positioned parallel to said outer sleeve.

4. The assembly of claim 3, wherein said outer sleeve comprises a groove that accommodates said elongated guide.

5. The assembly of claim 1, wherein said slots are configured at substantially every 2 millimeters on said outer sleeve.

6. The assembly of claim 1, wherein said tip comprises a plurality of appendages.

7. The assembly of claim 1, wherein said inner sleeve controls a depth of a drill insertion into a bone.

8. The assembly of claim 1, wherein said inner sleeve comprises a stop that engages said slots of said outer sleeve.

9. The assembly of claim 1, wherein said spring provides spring loading for said inner sleeve.

10. The assembly of claim 8, wherein said stop is located at a position of said middle portion of said inner sleeve that is adjacent to said tip of said inner sleeve.

11. The assembly of claim 3, further comprising a handle mounted over said second one of said straight ends of said shaft.

12. The assembly of claim 1, wherein said inner sleeve and said outer sleeve each comprise cleaning holes.

13. An assembly comprising:
an S-shaped shaft comprising a first straight end, a second straight end having a length longer than said first straight end, a curved portion adjoining said first straight end with said second straight end, and an elongated guide parallel to said first straight end and outwardly protruding from said first straight end;
a handle connected to said second straight end of said shaft;
a pin that connects said handle to said second straight end of said shaft;
an outer sleeve comprising slots configured in said outer sleeve, wherein said outer sleeve is connected to said shaft, wherein said outer sleeve is positioned parallel to said elongated guide of said first straight end of said shaft;
a tip connected to said outer sleeve, wherein said tip comprises a plurality of appendages;
an inner sleeve slidably mounted in said outer sleeve and controls a depth of a drill insertion into a bone, wherein said inner sleeve comprises a top end having a first diametrical configuration and a first length, a middle portion having a second diametrical configuration smaller than said first diametrical configuration and a second length longer than said first length, and a bottom end having a third diametrical configuration smaller than said second diametrical configuration and a third length shorter than said first length, wherein said middle portion comprises a stop; and
a spring adapted to provide spring loading for said inner sleeve.

14. The assembly of claim 13, wherein said slots are configured at substantially every 2 millimeters on said outer sleeve.

15. The assembly of claim 13, wherein said handle mounts over said second straight end of said shaft.

16. The assembly of claim 13, wherein said stop of said inner sleeve engages said slots of said outer sleeve.

17. The assembly of claim 13, wherein said inner sleeve and said outer sleeve each comprise cleaning holes.

18. The assembly of claim 13, wherein said stop prevents over-drilling in said bone.

19. The assembly of claim 13, wherein said appendages on said tip prevent slippage of said tip on a bone surface.

20. A method of controlling a depth of a drill insertion into a bone using a variable depth drill guide assembly comprising an S-shaped shaft comprising a curved portion; a pair of straight ends connected by said curved portion; and an elongated guide outwardly projecting along a substantially entire length of a longitudinal axis of a first one of said straight ends; an outer sleeve connected to said elongated guide of said shaft, wherein said outer sleeve comprises slots; a tip connected to said outer sleeve; an inner sleeve mounted in said outer sleeve and comprising a top end having a first diametrical configuration and a first length, a middle portion having a second diametrical configuration smaller than said first diametrical configuration and a second length longer than said first length, and a bottom end having a third diametrical configuration smaller than said second diametrical configuration and a third length shorter than said first length, wherein said middle portion comprises a stop; and a spring engaging said inner sleeve and said outer sleeve, said method comprising:
simultaneously depressing and rotating said top end of said inner sleeve until said stop of said middle portion of said inner sleeve mates with a corresponding slot in said outer sleeve;
pushing said tip into said bone;
inserting a drill into said inner sleeve;
said drill contacting said inner sleeve as said drill approaches a final position within said inner sleeve;
said inner sleeve resisting force asserted by said drill; and
said force overcoming the resistance from said inner sleeve.

* * * * *